United States Patent
Weibel-Furer et al.

(10) Patent No.: US 8,721,613 B2
(45) Date of Patent: May 13, 2014

(54) CONTAINER WITH HOLLOW NEEDLE

(75) Inventors: Ludwig Weibel-Furer, Waldstatt (CH); Dominique Weibel-Furer, Waldstatt (CH)

(73) Assignee: Vifor (International) AG, St. Gallen (CH)

(*) Notice: Subject to any disclaimer, the term of this patent is extended or adjusted under 35 U.S.C. 154(b) by 648 days.

(21) Appl. No.: 11/914,955

(22) PCT Filed: May 18, 2006

(86) PCT No.: PCT/EP2006/062415
§ 371 (c)(1), (2), (4) Date: Dec. 11, 2007

(87) PCT Pub. No.: WO2006/125747
PCT Pub. Date: Nov. 30, 2006

(65) Prior Publication Data
US 2008/0200886 A1    Aug. 21, 2008

(30) Foreign Application Priority Data
May 24, 2005 (EP) .................................. 05104386

(51) Int. Cl.
*A61J 1/05* (2006.01)
*A61J 1/20* (2006.01)

(52) U.S. Cl.
USPC ........................... 604/414; 604/411; 604/310

(58) Field of Classification Search
USPC ......... 604/403, 404, 407, 411, 412, 414, 415, 604/239, 110
See application file for complete search history.

(56) References Cited

U.S. PATENT DOCUMENTS

| | | | |
|---|---|---|---|
| 2,512,568 A * | 6/1950 | Saffir | 604/239 |
| 2,693,183 A * | 11/1954 | Lockhart | 604/201 |
| 2,757,671 A * | 8/1956 | Haafkens | 604/200 |
| 2,986,141 A * | 5/1961 | Hart | 604/206 |
| 3,114,369 A | 12/1963 | Hall | |
| 3,989,045 A | 11/1976 | Van Eck | |
| 4,328,912 A | 5/1982 | Haggar et al. | |
| 4,482,585 A * | 11/1984 | Ohodaira et al. | 428/35.2 |
| 4,505,709 A * | 3/1985 | Froning et al. | 604/411 |
| 5,261,881 A * | 11/1993 | Riner | 604/110 |
| 5,454,409 A * | 10/1995 | McAffer et al. | 141/329 |
| 5,545,375 A * | 8/1996 | Tropsha et al. | 422/102 |
| 6,379,342 B1 | 4/2002 | Levinson | |
| 6,706,031 B2 * | 3/2004 | Manera | 604/411 |
| 2003/0010795 A1 * | 1/2003 | Duqueroie | 222/212 |
| 2003/0015605 A1 | 1/2003 | Garcia et al. | |

OTHER PUBLICATIONS

International Search Report for PCT/EP2006/062415 mailed Aug. 17, 2006, three pages.

* cited by examiner

*Primary Examiner* — Susan Su
(74) *Attorney, Agent, or Firm* — Rankin, Hill & Clark LLP

(57) ABSTRACT

The present invention relates to a container (1, 1', 1") for the intake and release of a medicament, in particular a parenteral medicament, the container (1, 1', 1") exhibiting a casing (6, 6') which is sealed, except for an opening (7) for the purpose of releasing the medicament, the container (1, 1', 1") being designed in such a way that a release of the medicament is effected by alteration of at least one region of the casing (6, 6'). The casing (6, 6') is furthermore formed in one piece. The container exhibits a hollow needle (9, 10).

10 Claims, 3 Drawing Sheets

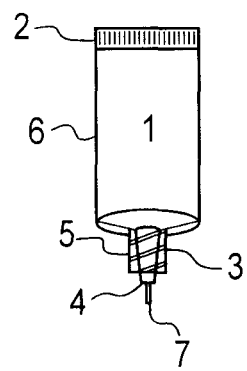
FIG. 1a
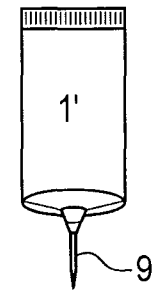
FIG. 1b
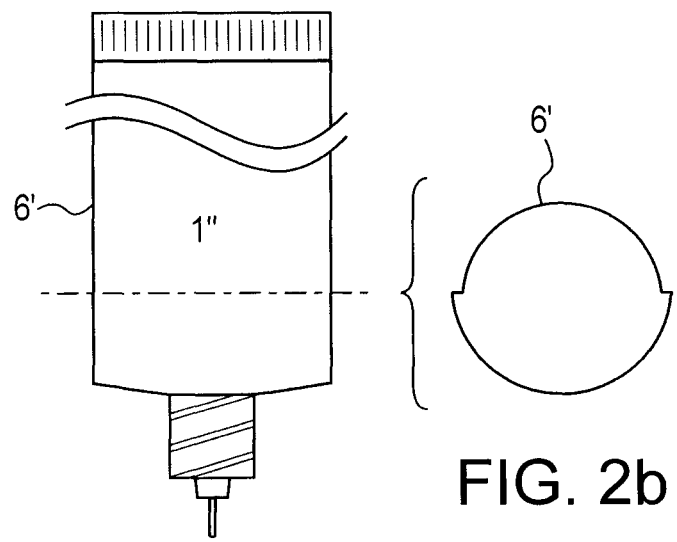
FIG. 2a
FIG. 2b

CONTAINER WITH HOLLOW NEEDLE

The present invention relates to a container for the intake of a medicament and the release thereof into an administration device, to the production and use of said container, and also to the associated administration device. The medicaments are, for example, medicaments to be administered parenterally, but they may also be oral or topical medicaments. The container according to the invention exhibits a particularly advantageous configuration of the casing.

In the case of parenteral administration—i.e. administration by-passing the gut of a mammal—of medicaments, this generally takes place by injection or infusion. The term 'injection' is understood to mean the administration of a liquid sterile medicament by means of a syringe and a hollow needle directly into the tissue or vascular system, by-passing the gastro-intestinal tract. In the case of infusion, it is a question of slow, mostly dropwise influx of relatively large quantities of (drug-containing) liquid into the body.

Medicaments—for example, medicaments to be administered parenterally—are generally decanted, after their preparation, into a container that is able to receive one or more portions/doses. This container is designated as the primary packing.

By way of primary packing, glass ampoules are known that have to be opened with a special ampoule saw or that are furnished with a predetermined breaking-point for the purpose of opening. The contents have to be transferred from the ampoule into a container that is suitable for the administration, such as a syringe, for example. Furthermore, for the most part, residual liquid has to remain in the ampoule, since otherwise the aspiration of air may occur disadvantageously in the course of filling the syringe. Moreover, a later sealing of the ampoule, with the residual liquid contained therein, is practically impossible.

A so-called pierceable ampoule (vial) is known from the state of the art as a further container. Said ampoule is punctured with a syringe at a point provided for this purpose, and the syringe is then filled with the liquid held in the container. This process associated with this container is very elaborate, since the ampoule cannot be used immediately for the purpose of administration, but the contents rather have to be transferred out of the ampoule into a container that is suitable for the administration, such as the aforementioned syringe. The opening or piercing of ampoules, and a subsequent necessary transfer into a container that is suitable for the administration, proves to be disadvantageous, for example in emergency situations in which administration has to be effected under time-pressure.

Nowadays, decanting is also effected directly into a syringe that is furnished with a clipped-on or glued-in cannula for the purpose of administration. By virtue of pressure on the plunger which is movably supported in the syringe container, the liquid is injected out of the container through the cannula into the place of administration. The syringe has the disadvantage that, by reason of the multi-part structure, it is comparatively expensive. For the purpose of maintaining operational capability also after a relatively long period of storage, the plunger and the syringe container are furnished with coatings, for example with silicone. Hence a substance is stored and administered together with the medicament that has nothing to do with the actual action of the medicament and that may even have a disadvantageous effect, for example in the case of medicaments having a high pH value.

Together with the parenteral medicaments—which in general are decanted into ampoules, vials or ready-to-use syringes, and also into infusion bottles or infusion bags—non-parenterally administered medicaments are sometimes also stored in ampoules or vials, since, for example, they have to be mixed with water prior to administration.

From U.S. Pat. No. 4,926,915 a container is known in the form of a collapsible tube. The collapsible tube disclosed therein represents a simplification of the ampoule or pierceable ampoule, since a syringe can be directly attached and filled. By way of means for connection to a collapsible tube, a surface is proposed tapering conically inwards to a point.

GB 800 455 A discloses the connection of two collapsible tubes so as to result in a reciprocal ejection of contents. Connection to an administration device is not provided.

U.S. Pat. No. 4,926,915 A discloses, inter alia, a collapsible-tube-shaped container with a Luer coupling for connection to an ampoule. Connection to an administration device is likewise not provided.

In US 2003/0010795 A1 a container is shown that is configured in such a way that a triggered release of a liquid is continued independently.

U.S. Pat. No. 4,328,912 describes a collapsible container that is capable of implementing a release of a liquid independently by reason of a specific design of a valve.

US 2003/0015605 A1 describes a container filled with a liquid, wherein under the influence of pressure a discharge is triggered abruptly only after an initial resistance has been overcome.

Against the background of the disadvantages described above, it is therefore the object of the present invention to make available a container for the intake and release of a medicament or, to be more exact, a container with an associated administration device that each facilitate the administration of a medicament and also the connection to an administration device and that are of comparatively simple construction.

This object is achieved by means of the container claimed in Claim 1. Advantageous configurations will become apparent from the dependent claims. An advantageous production process and also an advantageous use are subjects of the associated independent claims.

The container according to the invention for receiving and releasing a medicament is furnished with an integral casing which is sealed, except for an opening for the purpose of releasing the medicament. The container is furthermore configured in such a way that a release of the medicament from the opening is effected by alteration of the whole casing or of a region of the casing. The medicament is present, for example, in a solution or other liquid, the viscosity of which may have been chosen to be variable. For example, it is a question of a medicament to be administered parenterally, orally or topically.

In accordance with the invention, the alteration of the casing is associated with the release of the medicament. For example, by reason of the choice of material and, in particular, in the case of a comparatively large-volume casing the casing is configured to be collapsing; this means that at the time of release of the medicament by means of capillary forces and/or by reason of the effect of gravity the at least partial collapse of the casing, and consequently alteration of the casing, occurs by reason of the partial vacuum forming in the container.

The concept of 'integrality' is to be understood in such a way that the casing is not of multi-part construction. The casing is, for example, made of one material or several materials and/or exhibits differing compositions in various regions. In comparison with a multi-part structure, as in the case of a plunger device, the integrality of the casing ensures an inexpensive production of the device. Furthermore, administration is effected in a manner that is particularly simple, sterile, rapid and not susceptible to faults. By reason of the integrality, the number of product-contacting elements or materials is reduced, for example in comparison with a structural design having a moving plunger, so that the compatibility with the medicament can be ensured advantageously and comparatively simply.

The container according to the invention further includes a hollow needle in the region of the opening. In one embodiment, the hollow needle serves as means for connection to an administration device or to a container for a medicinal liquid. By means of the hollow needle the connection can be made quickly and securely. In the case of the administration devices to which a liquid-conducting connection is to be established by means of the needle, it is a question of means for infusion or injection that, for example, exhibit a membrane or foil which is penetrated by the hollow needle for the purpose of emptying the container into the administration device.

In an advantageous configuration of the device according to the invention, it is a question of an administration device—that is to say, an infusion or injection needle or cannula—that serves for administering the medicament to a patient via the opening. If the container that is used for transport and storage is used at the same time for the purpose of administering the medicament, a process of transfer from a transport container into a container that is intended for the administration is advantageously dispensed with.

In one configuration, the hollow needle serves for direct administration, for example by injection. Injection is effected—depending on the place of administration—intracutaneously, subcutaneously, intramuscularly, intravenously, intra-arterially, intracardially, intra-articularly, intrathecally or intralumbarly. In one embodiment, the hollow needle is manufactured from metal—for example, medical special steel—and is sharpened, in order to be employed as an injection or infusion needle in humans or animals.

According to one embodiment, the hollow needle is inserted or glued into the casing in the region of the opening.

According to another advantageous embodiment, the casing is formed integrally with the hollow needle. By virtue of this, the container can be produced particularly inexpensively. As a result, in advantageous manner no further material comes into contact with the medicament in the course of release of the medicament. During storage and release, contact with the medicament is limited to one material or one material composition. In this way it can be ensured particularly simply that contact with materials of the container does not have a disadvantageous effect—for example, altering the pH value—on the medicament contained in the container. Furthermore, in this way the container can be produced particularly simply, cost-effectively and rapidly, which is an advantage from the point of view of production technology.

In another advantageous configuration of the container according to the invention, said container is configured in such a way that the release of the medicament is achieved or at least triggered by pressure on at least one outer region of the casing. For example, the casing is designed in such a manner that a release of the medicament is brought about by pressure of the thumb on the associated outer region of the casing. As a result, a particularly reproducible, dosed release of the medicament—which, for example, is present in liquid form with highly varying viscosity—is made possible. For example, the injection pressure required for an injection is generated by the pressure acting on the casing; additional means for generating pressure—for example, a pump—can consequently be dispensed with advantageously. For example, the container is of tubular construction. A pressure on the tubular casing triggers a reduction in volume. The associated reduction in volume brings about a displacement out of the container of the medicament received in the container, and hence an escape and hence a release via the opening. Depending on the chosen hardness of the casing, the characteristic of the pressure to be applied can be advantageously varied.

In another advantageous embodiment, the container is configured in such a way that after the triggering of the release by virtue of the pressure the release of the medicament is continued independently. For example, this is achieved by means of a configuration in which, when a certain outer curvature is attained, a relatively hard and elastic casing segment jumps in spring-like manner—in accordance with the jumping-jack principle—into the opposite curvature, pointing into the interior of the container, and in this way releases a precisely defined volume of medicament by reason of the spring characteristic of the casing segment. By virtue of this, on the one hand an independent release is achieved, and on the other hand a well-dosed release.

According to another advantageous embodiment, the container exhibits a collapsible-tube-shaped casing. "Collapsible-tube-shaped" in the sense of the invention is to be understood in such a way that, substantially as a consequence of the heat sealing, the container tapers to a point at its end located opposite the opening. By virtue of this type of configuration, a particularly easy emptying of the container—and hence release of the medicament—is achieved. For example, by means of a stroking movement from the pointed end of the collapsible tube a particularly effective—i.e. rapid and largely remainder-free—emptying of the container can be achieved, particularly if the medicament exhibits a high viscosity in comparison with aqueous solutions. A collapsible tube is generated, for example, by means of a tube in which one end is sealed by flat heat sealing or folding, depending on the material being used in each instance. In one configuration, the access—existing prior to the heat sealing or folding—to the interior of the collapsible-tube-shaped container advantageously serves in addition as a supply option for the filling with the medicament which is subsequently received within the container and which is optionally released via the opening that is provided in accordance with the invention.

According to another advantageous embodiment, connection means are provided for detachable connection of the hollow needle to the container. The detachability enables the container to be detached from the administration device, in order, for example, to be able to attach a new filled container quickly. For example, for the purpose of detachable connection an extension furnished with an external thread is provided on the container, in which extension the opening is arranged concentrically. The hollow needle exhibits, for example, a recess interacting with the extension and receiving the latter. By virtue of the internal thread provided in the recess and interacting with the external thread, a detachable but simultaneously liquid-tight connection between the container and the hollow needle is achieved. The detachability, according to the configuration, of the connection between the container and the hollow needle ensures that a container can be easily exchanged for a filled container, as a result of which the flexibility and rapidity of administration and hence the user-friendliness are enhanced.

In another advantageous embodiment, the means for connecting the opening to the administration device include a locking means for preventing an unintentional loosening of the connection. For example, a screw device is furnished with a latching function which additionally secures the screw connection in the screwed-in state by means of a latching spring element. A loosening is possible only after this spring action, associated with the latching, has been overcome. An unintentional loosening of the connection is largely prevented in this way.

According to another advantageous embodiment of the container according to the invention, the means for detachable connection exhibit two conically-shaped surfaces complementary to one another. As a result, a simple and—at the same time—sufficiently tight connection is achieved. The container is preferably furnished with an extension having an outer surface tapering conically to the opening.

According to one embodiment, it is a question of a Luer coupling (Luer cone or Luer lock). A so-called Luer coupling is defined in ISO 594/1. In general, it is a question of a coupling designated as male. By provision of such a coupling on the container, several working steps are eliminated in the course of administration of the medicament.

According to another advantageous configuration, the connection means are formed, at least partially, integrally with the container. By virtue of this, the container can be produced particularly simply, cost-effectively and quickly, which is an advantage from the point of view of production technology.

Integrality is achieved, for example, in a single production step or as follows: in a first step of the production, two pieces are produced which are subsequently heat-sealed or joined together. The decanter is then furnished with an integral part, in order to fill this with the medicament. If use is made of existing injection moulds, a bringing-together of two parts is an advantage in the case of a production process where plastic hoses or laminate hoses which form the actual container are heat-sealed onto a head part with the connection means or if the connection means exhibit a particular complexity.

In another advantageous configuration, the container exhibits a volume of less than 5 ml. A volume of less than 5 ml proves to be particularly advantageous, since a container, in particular a collapsible tube, can be emptied efficiently and uniformly in one stroke by simple pressure with the thumb. It has become evident that, as a result, the handling of the container, and hence the administration of the medicament, is particularly simple and efficient.

In another advantageous embodiment, the container consists of synthetic material, in particular polypropylene, PE, such as LDPE or PET. Also usable are PVC, PVF etc. Nowadays, new, heat-sealable synthetic materials are also being developed that can be employed advantageously for medicaments. The choice of synthetic materials according to the invention is restricted only to the extent that the producibility of the container according to the invention is guaranteed. As a result, the container can be produced inexpensively. Furthermore, by reason of the comparatively low heat-sealing and melting temperature, sealing of the container after decanting has taken place can be effected in a manner that is particularly non-damaging to the medicament. Moreover, in this way the batch information and/or expiry information can be easily stamped onto the outer surface of the container. These inscriptions accordingly have a long life.

In another advantageous embodiment, the container consists of a laminate. As a result, there are further compatibility options. For example, an aluminium foil which itself does not touch the product but constitutes a heightened oxygen barrier may be inserted into the jacket of the container, and in this way the stability of the product is influenced favourably. Furthermore, preprinted labels, which for their part may again have a barrier function, may be inserted into the jacket (in-mould labelling). By virtue of this, even the affixing of labels is dispensed with, and no adhesive becomes necessary that could get into the product by diffusion.

According to another advantageous embodiment, the container is designed to be at least partially transparent. As a result, the filling-level or the emptying can be advantageously monitored.

According to another advantageous configuration, the container is coated. For example, the inner surface of the casing in contact with the medicament is coated with a chemically neutral coating such as silicon oxide. By virtue of this, it is ensured that, by reason of the coating, the container achieves, in this respect, glass-like properties without exhibiting the disadvantages associated with glass: for example, risk of injury when opening glass ampoules and disposing of them, etc.

In another advantageous embodiment, the casing of the container is designed to be at least partially elastic. By virtue of this, it is ensured that when the pressure on the casing is removed the latter is able to regain its original shape and the container can be emptied intermittently, for example in several similar movements executed in succession. As a result, emptying can be effected particularly simply.

According to another embodiment, the means for connection may furthermore interact with a seal intended for them, so that a particularly easy sealing of the container according to the invention—in contrast, for example, to the ampoules described in the introduction—is achieved. The seal is, for example, a separate plastic injection-moulded part which is screwed or fitted onto the hollow needle previously described. In another embodiment, the seal is integrally connected to the casing and is produced together with the container in one processing step, in order to protect the medicament received in the container against contamination. By virtue of this, the container together with the seal can be produced simply and cost-effectively. The sealing means include, for example, screw or plug-in caps and segments that are heat-sealed onto the casing and furnished with predetermined breaking-points.

The process according to the invention for producing the container exhibits a step in which the container is produced in a plastics injection-moulding step, plastics injection-blow-moulding step or plastics extrusion-blow-moulding step. As a result, the container can be produced inexpensively, optionally together with the seal and/or the means for detachable connection to the administration devices. In another production process the jacket and the head part are produced separately and are heat-sealed to one another. Furthermore, the integrality that is advantageous for the decanter and user can be achieved by two parts being produced separately by the manufacturer but being already assembled (e.g. stuck together and subsequently heat-sealed) to form one piece by said manufacturer.

WITH REFERENCE TO THE FIGURES

FIGS. 1a and 1b show exemplary embodiments of the container according to the invention.

FIGS. 2a and 2b show a form of the container according to the invention, wherein regions of the casing are themselves constructed in collapsing manner.

Figure 3:
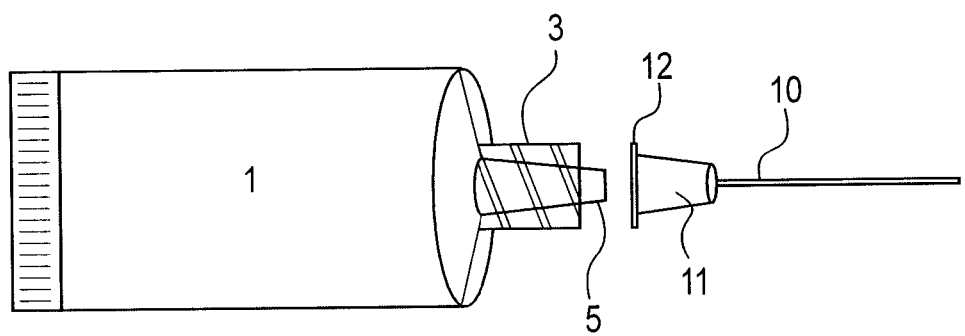

FIG. 1a shows a first embodiment of the container 1 according to the invention with a collapsible-tube-shaped, one-piece casing 6. A liquid (not represented) containing a medicament (in general, a parenteral medicament) is contained in the casing 6. The (in general, parenteral) medicament or, to be more exact, the liquid is released from the container 1 via the opening 4 by pressure being exerted on the casing 6 in the region of 1, for example with the fingers. The casing 6 is sealed in airtight and liquid-tight manner on the side located opposite the opening 4 by a heat seal 2 extending in plane manner, as a result of which the collapsible-tube shape arises. The means of connection of the opening 4 of the container to an administration device which is not shown include a conical extension 5 formed on the casing. The contour of said extension is indicated in FIG. 1a by dashes, since it is partially surrounded by a sleeve 3 furnished with an internal thread, which is likewise part of the connection means. The conical extension may have been provided without the sleeve, and consequently forms a so-called Luer male coupling. If the sleeve has been provided with an internal thread, a structure arises that corresponds to a so-called Luerlock coupling. The conically extending extension 3 as part of the connection means serves, with connection of a connecting element complementary thereto, for an infusion needle or injection needle by way of administration device (not represented in the illustration), in order to connect said device, on the one hand, in liquid-conducting manner and, on the other hand, tightly and detachably.

The opening 4 is, for example, sealed at the outlet with a predetermined breaking-point, in which connection an arbitrarily shaped breaking aid 7 is attached by injection moulding, or with a directly cast-on foil or membrane which, for example, can be penetrated with a pointed object.

FIG. 1b shows another embodiment 1' of the collapsible-tube-shaped container according to the invention. Said container differs from the embodiment 1, above all, by virtue of the different design of the casing in the region of the opening. Furthermore, the hollow needle 9 according to the invention is shown which serves for connection of the container to an administration device—that is to say, for the introduction of said container into an infusion bag, for example. The hollow needle is formed integrally with the casing.

FIGS. 2a and 2b show another embodiment 1" of the container according to the invention. Said container is furnished with a casing 6' which at the time of release of the medicament utilises the jumping-jack principle. In FIG. 2b the casing 6' is represented in section. The upper half of the casing shown in the Figure jumps elastically inwards after a certain curvature has been exceeded after initial external pressure; this inwardly directed spring action brings about a displacement effect on the medicament held in the casing 6', and results in a release of the medicament via the opening. By reason of the predetermined spring action, a release is brought about in reproducibly independent manner after the first, triggering pressure on the casing 6'. Consequently the same quantity of liquid is always ejected. In cross-section it is evident that the upper half of the casing fits into the other half after pressure and so is also no longer able to spring back into its original shape.

FIG. 3 shows the embodiment that is shown in FIG. 1 with associated infusion needle or injection needle 10. The connection means 12 attached to the infusion needle or injection needle 10 exhibits an inner surface which tapers conically inwards to a point in such a manner that it is complementary to the outer surface 5 of the connection means of the container 1. By engagement of the two surfaces of the connection means 5, 12, a detachable connection between the container 1 and the needle 10 is established. This connection is additionally fixed by means of a screw connection between the internal thread of the casing 3 and the external thread 12 provided on the connecting part 11 of the needle.

Figure 4:
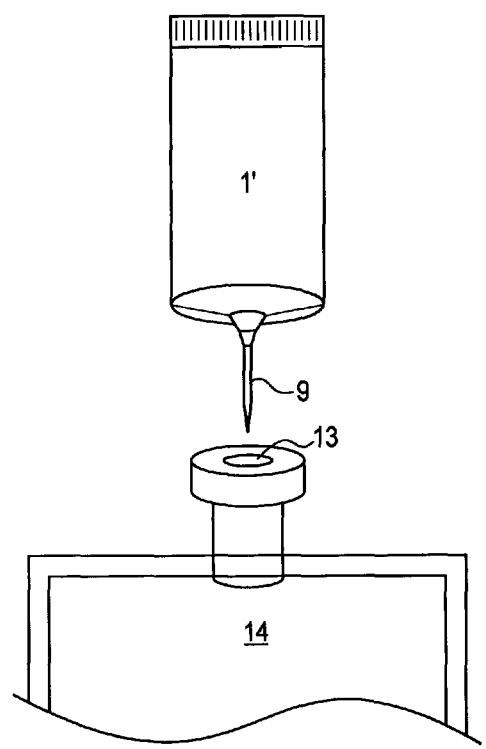

FIG. 4 shows the use of the container 1' from FIG. 1b. The hollow needle 9 serves for connection to an infusion bag or infusion bottle 14, whereby a foil or membrane 13 of the infusion bag or infusion bottle 14 is penetrated, in order to introduce the medicament held in the container 1' into the bag or bottle 14.

The invention claimed is:

1. A method for release of a parenteral medicament, the method comprising:
    (a) providing a container containing the parenteral medicament, wherein the container has a volume of less than 5 ml and wherein the container comprises
        (i) a one-piece casing which is sealed, except for an opening for the purpose of releasing the medicament, wherein the at least a portion of the casing of the container is at least partially collapsible, wherein the container is used for transport, storage, and administering of the medicament, and wherein release of the medicament is effected by alteration of at least one outer region of the casing and
        (ii) a hollow needle in the region of the opening, wherein the hollow needle is formed integrally with the casing,
    (b) altering the at least one outer region of the casing such that the medicament is released from the container through the hollow needle and the opening;
    (c) applying pressure to the at least one outer region of the casing in order to reproducibly trigger the release of a dose of the medicament; and
    (d) continued independent release of the medicament following the pressure-triggered release,
    whereby during release of the medicament, the medicament does not contact any other materials besides that of the hollow needle and the casing
    wherein the hollow needle connects to an administration device;
    wherein the administration device comprises a membrane or foil, the method further comprising causing the needle to penetrate the membrane or a foil for the purpose of emptying the container into the administration device;
    wherein the container is attached to the administration device by the hollow needle to form a connection between the container and administration device;
    wherein the hollow needle interacts with a seal intended for it so that a sealing of the container is achieved; and
    wherein the seal is integrally connected to the casing of the container.

2. The method of claim 1, wherein the hollow needle includes a lock for preventing an unintentional loosening of the connection.

3. The method of claim 1, wherein the hollow needle includes a Luer coupling.

4. The method of claim 3, wherein the hollow needle is formed, at least partially, integrally with the container.

5. The method of claim 3, wherein the container is emptied in one stroke by application of manual pressure to the outer region of the casing.

6. The method of claim 5, wherein the container is at least partially transparent.

7. The method of claim 5 wherein the container further comprises a coating of silicon oxide.

8. The method of claim 1, wherein the container comprises a laminate.

9. The method of claim 1, wherein the container is emptied in one stroke by application of manual pressure to the outer region of the casing.

10. A method for release of a parenteral medicament, the method comprising:
    (a) providing a container containing the parenteral medicament, wherein the container comprises:
        (i) a one-piece casing which is sealed, except for an opening for the purpose of releasing the medicament, wherein the at least a portion of the casing of the container is at least partially collapsible, wherein the container is used for transport, storage, and administering of the medicament, and wherein release of the medicament is effected by alteration of at least one outer region of the casing and (ii) a hollow needle in the region of the opening, wherein the hollow needle is formed integrally with the casing, (b) altering the at least one outer region of the casing such that the medicament is released from the container through the hollow needle and the opening;

(c) applying pressure to the at least one outer region of the casing in order to reproducibly trigger the release of a dose of the medicament; and (d) continued independent release of the medicament following the pressure-triggered release, whereby during release of the medicament, the medicament does not contact any other materials besides that of the hollow needle and the casing wherein the hollow needle connects to an administration device;

wherein the administration device comprises a membrane or foil, the method further comprising causing the needle to penetrate the membrane or a foil for the purpose of emptying the container into the administration device;

wherein the container is attached to the administration device by the hollow needle to form a connection between the container and administration device;

wherein the hollow needle interacts with a seal intended for it so that a sealing of the container is achieved; and wherein the seal is integrally connected to the casing of the container.

* * * * *